(12) United States Patent
Lindeberg

(10) Patent No.: US 8,230,747 B2
(45) Date of Patent: Jul. 31, 2012

(54) CELL FOR TESTING FLUIDS AT ELEVATED PRESSURES

(75) Inventor: Erik Gøsta Bruno Lindeberg, Trondheim (NO)

(73) Assignee: Sinvent AS, Trondheim (NO)

( * ) Notice: Subject to any disclaimer, the term of this patent is extended or adjusted under 35 U.S.C. 154(b) by 626 days.

(21) Appl. No.: 11/991,006

(22) PCT Filed: Aug. 31, 2006

(86) PCT No.: PCT/NO2006/000307
§ 371 (c)(1),
(2), (4) Date: Apr. 2, 2009

(87) PCT Pub. No.: WO2007/027099
PCT Pub. Date: Mar. 8, 2007

(65) Prior Publication Data
US 2009/0211364 A1  Aug. 27, 2009

Related U.S. Application Data

(60) Provisional application No. 60/712,419, filed on Aug. 31, 2005.

(51) Int. Cl.
*G01L 7/16* (2006.01)
(52) U.S. Cl. ............................. 73/744; 73/708; 92/171.1
(58) Field of Classification Search .................... 73/744, 73/736, 715, 708
See application file for complete search history.

(56) References Cited

U.S. PATENT DOCUMENTS

| 3,183,722 | A | * | 5/1965 | Unger et al. .................... 73/744 |
| 4,658,637 | A | | 4/1987 | Ollivaud et al. |
| 5,126,058 | A | | 6/1992 | Beckman |
| 5,370,043 | A | * | 12/1994 | Traff et al. ...................... 99/467 |
| 6,879,166 | B2 | | 4/2005 | May et al. |
| 2003/0155926 | A1 | | 8/2003 | May et al. |

FOREIGN PATENT DOCUMENTS

| EP | 0 180 844 | 5/1986 |
| GB | 2 346 669 | 8/2000 |
| WO | 02/01211 | 1/2002 |

OTHER PUBLICATIONS

International Search Report mailed Dec. 12, 2006 for International Application No. PCT/NO06/000307.
International Preliminary Report on Patentability mailed Mar. 13, 2008 for International Application No. PCT/NO2006/000307.
Written Opinion of the International Searching Authority mailed Dec. 12, 2006 for International Application No. PCT/NO2006/000307.

* cited by examiner

*Primary Examiner* — Lisa Caputo
*Assistant Examiner* — Roger Hernandez-Prewitt
(74) *Attorney, Agent, or Firm* — Wenderoth, Lind & Ponack, L.L.P.

(57) ABSTRACT

An apparatus for a burst safe pressure-neutral high pressure cylinder in pVT and condensate cells is described. The dimensions of an outer cylinder are such as to prevent plastic flow of the inner cylinder wall caused by elevated inside pressure and/or temperature.

6 Claims, 1 Drawing Sheet

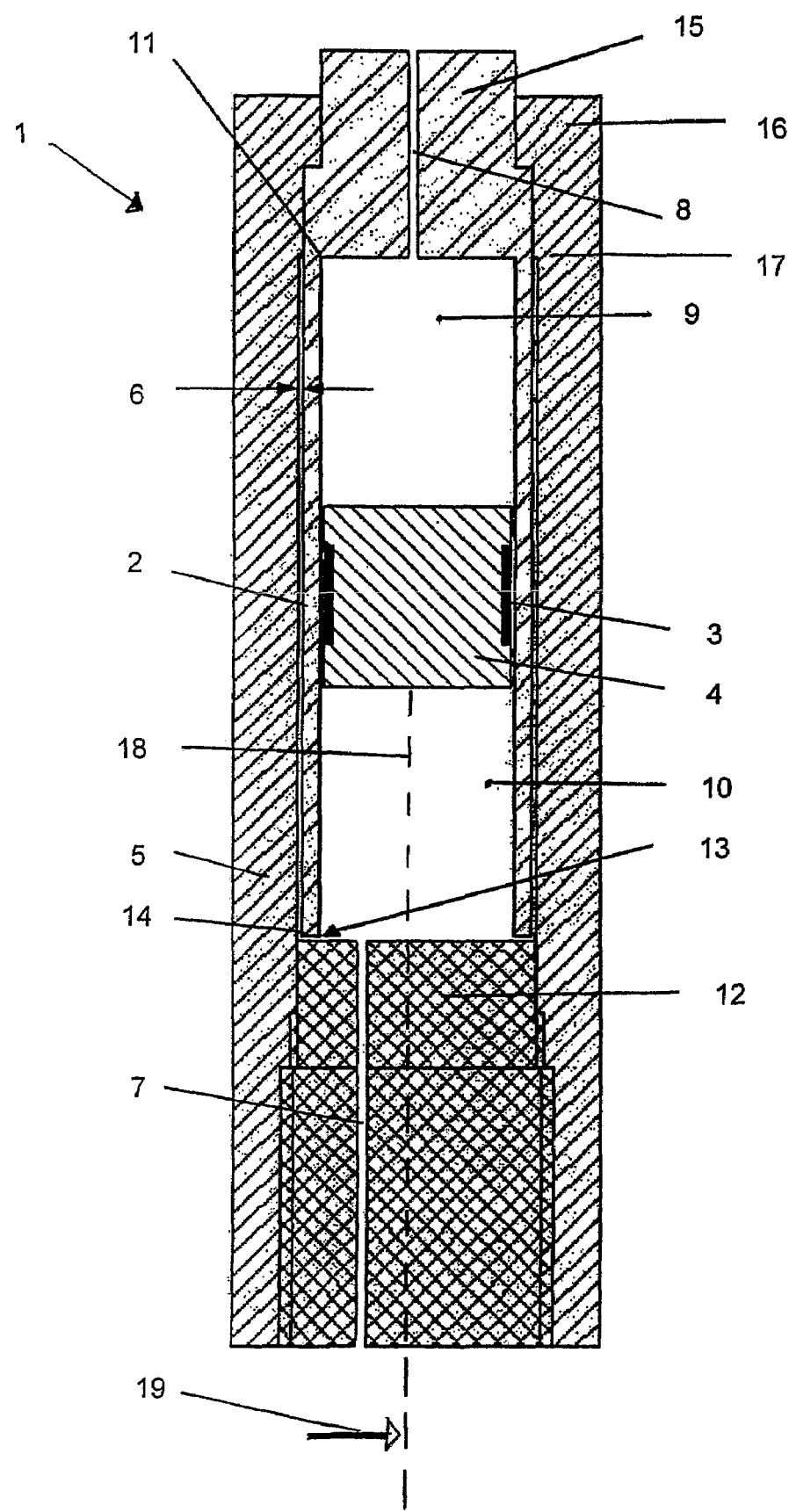

CELL FOR TESTING FLUIDS AT ELEVATED PRESSURES

The present application hereby claims priority to U.S. Provisional Application No. 60/712,419, filed Aug. 31, 2005.

BACKGROUND OF THE INVENTION

1. Technical Field

The present invention relates to a test cell for testing fluids at elevated pressures. More specifically, the test cell of the present invention comprises a pressure-neutral cylinder for use in pressure, volume and temperature (pVT) studies of reservoir fluids and their properties in the laboratory and in the field.

In pVT cells and condensate cells, petroleum fluids can be studied at varying pressure and temperature, simulating the conditions in oil reservoirs before and during production. Typically, these fluids contain gas. The change in fluid density (compressibility) and the tendency for the gas to come out of solution at decreasing pressure are of particular interest.

pVT cells are optimized to study oils with dissolved gas, while condensate cells are optimized to study light oils with a high gas to oil ratio. In the following, they are both denoted pVT cells.

2. Description of Related Art

Until the late eighties, the method for controlling the pressure in these pVT cells was to pump mercury in and out of the cell, mercury being considered as inert with respect to the petroleum fluids.

There were however some health risks involved in the handling of mercury at high pressure and temperature, and this method has to a large extent been replaced by other methods for changing the volume in pVT cells. Several of the new designs are based on cylindrical cells with a sealed piston that can be moved by either direct mechanical drive or hydraulic drive.

A problem with the piston solution is that the diameter of the cell will change with pressure, and thus the clearance between piston and wall will change, which makes rather high demands on the seals.

In order to solve the problem of varying clearance with pressure, a relatively thin inner cylinder, which is in contact with a dynamic seal on the piston and with the fluids, is enclosed in a thick-walled high pressure cylinder. The space between the cylinders is filled with hydraulic fluid, and is connected to the same line that provides such fluid under high pressure to hydraulically control the piston position. Thus it is ensured that the (differential) pressure across the inner cylinder is negligible.

This solution gives the following advantages:

1. The material of the inner cylinder can be selected independently to meet various specifications. The material of the inner cylinder (e.g. Hastelloy C, glass, Inconel) can be selected to be chemically compatible with the fluids while the outer cylinder needs only to be strong enough to meet the pressure specification (e.g. high strength steel) or a combination of weight and strength specifications (e.g. Ti-6A1-4V).

2. The diameter of the inner tube does not change with pressure, and the volume of the test fluid chamber is therefore only dependent on the position of the piston which can be monitored directly. This solution is applied in the so-called "DBR Jefri" cells with utilization of a pressure-neutral inner cylinder made of a glass material, and with external connection for the pressure outside the inner cylinder and the pressure behind the piston.

If the piston position accidentally is at the bottom of the cylinder, a pressure difference across the inner cylinder wall may occur due to elevated pressure in the inside test fluid (caused by temperature increase or charging with more test fluid), or by a falling pressure in the hydraulic system. This pressure difference might burst or cause plastic flow of the inner cylinder wall, depending on the cylinder material being brittle or ductile.

While the DBR solution provides a pressure-neutral inner cylinder and chemical compatibility with test fluids, both material deformation properties and clearances are such as to allow the inner cylinder to deform and/or break.

Hence, an alternative apparatus to those described above is needed to perform pVT studies without the risk and inconvenience of bursting or deforming the inner cylinder.

SUMMARY OF THE INVENTION

The present invention solves the problem of providing an improved pVT cell relative to the prior art cells.

In accordance with the present invention, the solution lies in providing a test cell for testing fluids at elevated pressures, which test cell comprises an inner cylinder inside which a piston is movable axially by hydraulic means to control pressure and volume of a fluid contained at a test fluid side of the piston, the inner cylinder having a thin cylinder wall and being closed at an end at the test fluid side, and an outer cylinder coaxially arranged outside the inner cylinder, thereby forming an annular space between the cylinders, the outer cylinder having a thick and sturdy construction, and at least one port for introducing hydraulic fluid to a hydraulic side of the piston opposite the test fluid side, and to the annular space.

The test cell of the invention is characterized in that the annular space has a radial dimension less than a maximum elastic expansion range of the inner cylinder, whereby rupture of the inner cylinder from a differential pressure across the cylinder wall can be avoided, due to restriction by the outer cylinder.

In order to provide a favorable and effective mounting procedure, as well as a simple layout for the hydraulic port arrangement for a test cell in accordance with the invention, the following preferable embodiment of the invention is provided: the outer cylinder is closed by a sealing plug having an axial clearance to an open end of the inner cylinder, thereby providing fluid communication between the hydraulic side inside the inner cylinder and the annular space. Hence, only one port for hydraulic fluid is necessary.

Further, in order to provide simple and effective means for measuring the test fluid volume, there is in another preferable embodiment provided an axially arranged piston rod attached to the piston and extending out of the cell through a sealed opening in an end closure, and past a measurement device for piston position.

BRIEF DESCRIPTION OF THE DRAWING

In the following, a more detailed explanation of the invention will be given with reference to FIG. 1, which shows a cross-section through a schematic (idealized) embodiment of a pVT cell in accordance with the present invention.

DESCRIPTION OF PREFERRED EMBODIMENTS

In FIG. 1 appears a pVT cell 1 in accordance with an embodiment of the present invention. A relatively thin inner cylinder 2 which is in contact with a dynamic seal 3 on a piston 4 and with a fluid 9 to be tested as well as a hydraulic fluid 10, is enclosed by a thick-walled high pressure cylinder 5. An annular space 6 between cylinders 2 and 5 is filled with hydraulic fluid, by connection to the same line 7 that controls the piston position. High pressure fluids 9 that are subjected to study are fed through a high pressure port 8 at the top of the cell 1.

The gap 6 between the inner and outer cylinders 2, 5 is so small that it is less than the limit for elastic deformation of the inner cylinder 2, so that the inner cylinder, on sudden expansion, will rest on the outer cylinder 5 before being damaged. The cell is therefore robust, and will not be damaged by deformation caused by inner pressure, even if the outer pressure drops significantly.

The reason for expansion of the inner cylinder 2, may be an inside overpressure, contained fluid elevated temperature or elevated temperature of fluid and/or surrounding outer cylinder material transferring heat to increase the temperature of the inner cylinder wall.

With further reference to FIG. 1, it appears that the test cell embodiment provides a burst- safe and pressure-neutral pVT cell with a cylindrical design. Innermost there is a slideable piston 4 that divides the inner cylinder space into an upper compartment for receiving high-pressure test fluid 9 therein, and a lower compartment for receiving hydraulic fluid 10 therein. The piston 4 can move inside a relatively thin-walled fluid container 2 that has a substantially uniform inside diameter and concentrically an equally uniform outside diameter. At the top end, this inner cylinder 2 is closed at a position 11 by an end closure 15 that is preferably integral with the thin-walled cylinder 2. There is a fluid port 8 through the end closure 15 for letting test fluid in and out of the test chamber above piston 4. When port 8 is closed, the volume and pressure of a fluid inside the top chamber is determined by the position of piston 4.

An outer cylinder 5 surrounds the thin-walled inner cylinder 2. The outer cylinder needs not necessarily have an outer shape that is cylindrical, but the inside shape must be a cylinder coaxial with the inner cylinder and with an inside diameter only somewhat larger than the outside diameter of the inner cylinder. Hence, what is essential is that there is a substantially uniform and coaxial circumferential clearance 6 between the two cylinders. This clearance 6 has the shape of an annular channel. This annular channel extends all the way along the length of the inner cylinder. In the embodiment shown, the outer cylinder 5 is provided with a small shoulder at the position indicated by reference numeral 17. Above that position, the outer cylinder 5 is joined tightly to the end closure 15 of the inner cylinder 2.

It is important that the radial dimension of the annular channel 6 is less than the elastic range of deformation of the inner cylinder 2. If the inner cylinder 2 is exposed to an overpressure from the inside, compared to the outside pressure, the wall of the inner cylinder 2 will tend to expand. The inner wall of the outer cylinder 5 will then restrict further expansion of the inner cylinder and save it from rupture.

In order to provide the same hydraulic pressure to fluid 10 both in the annular channel 6 and in the hydraulic pressure chamber underneath piston 4, it is possible to provide fluid communication between these two spaces such as indicated in the embodiment shown in FIG. 1, namely by providing a small axial clearance 13 between the lower end 14 of inner cylinder 2 and a sealing plug 12 just therebelow. The sealing plug 12 is a tightening member entered from below and fastened inside the outer cylinder 5.

In this embodiment, it is only necessary to have one port 7 for hydraulic fluid from a hydraulic pressure source (not shown), because the hydraulic fluid will enter the annular space 6 from the lower part of the cylinder interior.

However, in another embodiment, a closure element at the lower end of the cylinder interior may be attached to the inner cylinder 2 itself, or there may be no clearance between a sealing plug like plug 12 and the inner cylinder 2. In such a case, at least one further port for hydraulic fluid must be provided through outer cylinder 5 to the annular channel 6.

In principle, one might consider a further embodiment in which the end closure part 15 of the inner cylinder would be integrated with the outer cylinder 5 at area 16, so that the inner and outer cylinders would actually be in one piece, i.e. with the annular space 6 machined out from one "start cylinder" piece. However, such an operation is rather difficult, so the preferred embodiment is to have a separate inner cylinder 2 such as shown in the drawing, joined tightly together with the outer cylinder at top end 15, 16 by a thread connection. It appears that in a mounting operation, one would then preferably screw together the outer cylinder 5 and the inner cylinder 2 in the top area (15, 16, 17), and thereafter piston 4 would be entered into the inner space from below. Finally, an end plug 12 might be screwed tightly into the lower end of the outer cylinder. At the top end 16 of the outer cylinder, there is a shoulder inside for defining a stop for the first part of the mounting operation. Another shoulder at reference numeral 17 provides the axial dimension of the important annular channel 6.

FIG. 1 also shows an indication regarding a measurement apparatus for determining the position of the piston 4, and hence the volume of test fluid 9 in the top chamber. A dotted line represents a piston rod 18 attached to the underside of piston 4 and extending all the way out through the sealing plug 12. Hence, there is of course a thin through channel in plug 12, with seals so as to avoid leakage therethrough. The piston rod is sufficiently long to extend to a marker or reading device 19 even when the piston 4 is in a top position. The reading device 19 cooperates with markings on the piston rod 18 to establish piston position.

As regards materials, the material of the inner cylinder 2 would be selected not so much for strength, as for being chemically compatible with the fluids. Hence the previously mentioned materials Hastelloy C, glass or Inconel are candidate materials. The outer cylinder needs only be sufficiently strong to meet pressure specifications, e.g. high strength steel, or specifications regarding a combination of strength and weight, for instance Ti-6A1-4V.

In a practical example, the length dimension of a pVT cell such as appearing in FIG. 1, would be approximately 500 mm, the outer diameter would be variable within wide limits (as previously mentioned, the outer shape needs not even be cylindrical), but the outer diameter of the inner cylinder 2 might be approximately 50 mm while the wall of the inner cylinder 2 would be about 2 mm. The radial dimension of the annular channel 6 may typically be in the range 0.05 mm-1.0 mm. A typical axial dimension of the inner cylindrical space would be 200 mm, and the axial dimension of the piston 4 might be approximately 50 mm.

Neither the materials given as examples here, nor the dimensions given, should be construed as limitative regarding the scope of the present invention.

The invention claimed is:

1. A test cell for testing fluids at elevated pressures, comprising:

an inner cylinder having a piston inside thereof that is movable axially for controlling pressure and volume of a fluid on a test fluid side of said piston, said inner cylinder having a thin cylinder wall and being closed at an end of said inner cylinder on the test fluid side of said piston;

an outer cylinder coaxially arranged outside said inner cylinder so as to form an annular space between said outer cylinder and said inner cylinder, said outer cylinder having a thick and sturdy construction relative to said inner cylinder, and said outer cylinder having at least one port for introducing hydraulic fluid to a hydraulic side of said piston opposite to said test fluid side of said piston; and wherein said annular space has a radial dimension that is smaller than the maximum elastic expansion range of said inner cylinder such that rupture of said inner cylinder due to differential pressure across said thin cylinder wall is prevented by restriction of expansion of said inner cylinder by said outer cylinder.

2. The test cell of claim 1, wherein said outer cylinder is closed by a sealing plug that has an axial clearance with an open end of said inner cylinder so as to provide fluid communication between the inside of said inner cylinder on the hydraulic side of said piston and said annular space.

3. The test cell of claim 1, further comprising a piston rod that is attached to said piston, extending out of said outer cylinder through a sealed opening in an end closure of said outer cylinder, and a measurement device, past which said piston rod extends, for measurement of a position of said piston.

4. A test cell for testing fluids at elevated pressures, comprising:

an inner cylinder having a piston inside thereof that is movable axially in order to control pressure and volume of a fluid on a test fluid side of said piston, said inner cylinder being closed at an end of said inner cylinder on the test fluid side of said piston;

an outer cylinder coaxially arranged outside said inner cylinder so as to form an annular space between said outer cylinder and said inner cylinder and said outer cylinder having at least one port for introducing hydraulic fluid to a hydraulic side of said piston opposite to said test fluid side of said piston and to said annular space;

wherein said inner cylinder has a thin cylinder wall relative to the thickness of said outer cylinder; and wherein said annular space has a radial dimension that is smaller than the maximum elastic expansion range of said inner cylinder such that rupture of said inner cylinder due to differential pressure across said thin cylinder wall is prevented by restriction of expansion of said inner cylinder by said outer cylinder.

5. The test cell of claim 4, wherein said outer cylinder is closed by a sealing plug that has an axial clearance with an open end of said inner cylinder so as to provide fluid communication between the inside of said inner cylinder on the hydraulic side of said piston and said annular space.

6. The test cell of claim 4, further comprising a piston rod that is attached to said piston, extending out of said outer cylinder through a sealed opening in an end closure of said outer cylinder, and a measurement device, past which said piston rod extends, for measurement of a position of said piston.

* * * * *